United States Patent [19]

Koop et al.

[11] Patent Number: 5,243,399
[45] Date of Patent: Sep. 7, 1993

[54] ALIGNMENT TOOL FOR ENDOSCOPES

[75] Inventors: Dale Koop, Sunnyvale; Michael Arnett, Palo Alto, both of Calif.

[73] Assignee: Coherent, Inc., Palo Alto, Calif.

[21] Appl. No.: 821,978

[22] Filed: Jan. 15, 1992

[51] Int. Cl.⁵ .............................................. G01B 11/26
[52] U.S. Cl. .................................... 356/153; 356/241; 128/6
[58] Field of Search ................. 356/153, 241; 128/4, 128/6

[56] References Cited
U.S. PATENT DOCUMENTS 4,588,294  5/1986  Siegmund ........................... 356/241
4,902,129  2/1990  Siegmund et al. .................. 356/241

Primary Examiner—Vincent P. McGraw
Assistant Examiner—K. P. Hantis
Attorney, Agent, or Firm—Limbach & Limbach

[57] ABSTRACT

A tool is disclosed for evaluating the alignment of the channel of an endoscope. The tool includes a housing with one end thereof being connectable to the endoscope. The other end of the housing includes an eyepiece. A lens system is provided within the housing for imaging the distal end of the endoscope onto a reticle. The position of the image on the reticle allows the axial alignment of the endoscope channel to be evaluated.

6 Claims, 1 Drawing Sheet

ALIGNMENT TOOL FOR ENDOSCOPES

TECHNICAL FIELD

The subject invention relates to a tool for evaluating the axial alignment of the channel of an endoscope.

BACKGROUND OF THE INVENTION

An endoscope is an elongated tubular device for insertion into the body of a patient. The endoscope includes at least one central channel or bore which can be used, among other things, to view a tissue site within the body. The endoscope can include additional channels for suction, irrigation or to allow the insertion of small surgical instruments. The bore can also be used to transmit a beam of laser radiation for treating the tissue.

Although the subject invention is applicable to endoscopes generally, the remainder of the discussion will be often refer to laser laparoscopes as an example. A laser laparoscope is an endoscope which is used to deliver laser energy to a tissue site during laparoscopic surgery. The laparoscope includes at least one principle channel through which the beam from a surgical laser, typically a $CO_2$ laser, is passed.

FIG. 1 is an illustration of a typical laparoscope in conjunction with a laser system. The main barrel of the laparoscope 2 is approximately 13 to 17 inches in length. At least one channel 4 is formed within the laparoscope 2. Typically, a coupler 6 is connected to the proximal end of the laparoscope 2. The coupler 6 includes a lens system 8 for focusing the light from the laser into the channel 4.

Light from the $CO_2$ laser 10 is typically delivered to the laparoscope 2 through an articulated arm 12. The arm 12 includes a plurality of segments 14 connected by joints 16. The joints 16 include internal mirrors (not shown) for redirecting the light. The distal end of the arm 12 is configured to mate with the coupler 6.

As can be appreciated, during a surgical operation, it is necessary that the laser beam be accurately delivered from the laser, through the arm and laparoscope into the patient. Any axial deviations which exist in the laser, arm or laparoscope will prevent all of the light from reaching the patient. Accordingly, prior to beginning surgery, either the surgeon or the operating room nurse will assemble all of the delivery elements to see if the light is properly exiting the laparoscope. If the alignment is not correct, the surgery is often postponed because the operator has no way of knowing whether the misalignment is due to the laser, arm or laparoscope. Typically, both the endoscope company and the laser company (responsible for the laser and the arm) are called for service. As can be appreciated, it would desirable to have a simple tool which can be used to isolate any alignment problems in a laser delivery system.

Therefore, it is an object of the subject invention to provide a tool for assessing the alignment of the channel of an endoscope and coupler.

It is a further object of the subject invention to provide a tool connectable to an endoscope coupler which provides a visual indication of the alignment of the bores of the coupler and endoscope.

It is still another object of the subject invention to provide a tool which facilitates the adjustment of an endoscope coupler to maximize the delivery of laser energy through the endoscope.

SUMMARY OF THE INVENTION

In accordance with these and other objects, the subject invention provides a tool connectable to an endoscope. The tool includes a housing with one end thereof being configured to connect to the coupler of a endoscope. The other end of the tool includes a magnifying eyepiece. A lens system and a reticle are mounted within the housing. The lens system is designed to image the distal end of the endoscope on the reticle. If the endoscope channel is axially aligned, the image will be centered on the reticle. Any radial displacement of the image on the reticle will indicate that the channel is misaligned.

The subject tool is quick and easy to use such that it can be employed by hospital personal. An endoscope can be checked without the laser being connected or even present. Accordingly, the evaluation can be performed well before the surgery is scheduled to begin. If a problem is found in the endoscope, a replacement can be secured. If the endoscope is found to be aligned but the laser beam does not properly exit the endoscope, it can be inferred that the laser itself or articulated arm is misaligned. In the latter case, the laser company can be contacted.

A number of newer couplers are provided with adjustment mechanisms shown generically in FIG. 1 by the numeral 20. These mechanisms can include a joystick and mirror combination. If the endoscope is provided with such a mechanism, the subject tool can be used to adjust the lens system until the beam has been aligned down the channel of the endoscope.

Further objects and advantages of the subject invention will become apparent from the following detailed description taken in conjunction with the drawings:

DETAILED DESCRIPTION OF THE PREFERRED EMBODIMENT

Figure 1:
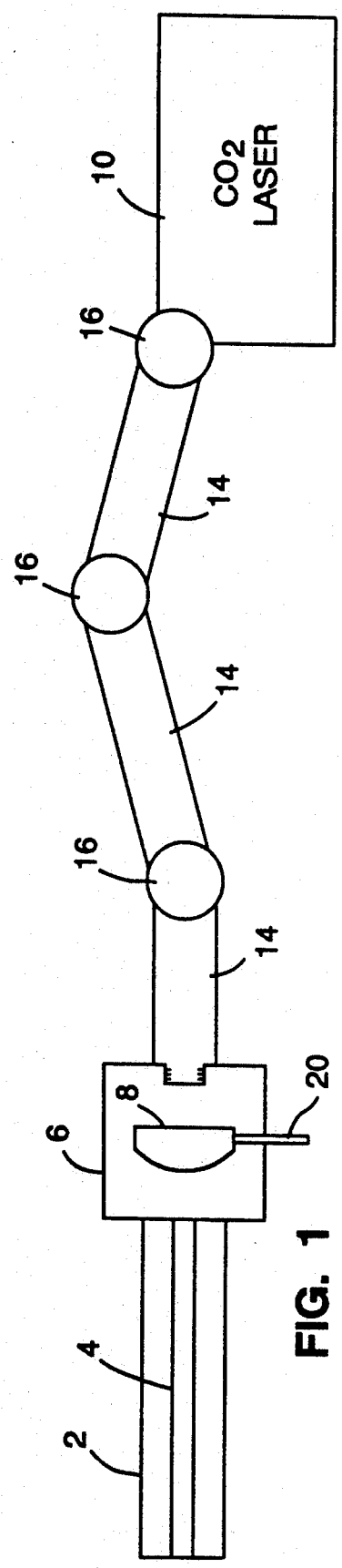
FIG. 1 is a schematic diagram of typical surgical laser system found in the prior art including a laser, articulated arm, coupler and endoscope.
Figure 2:
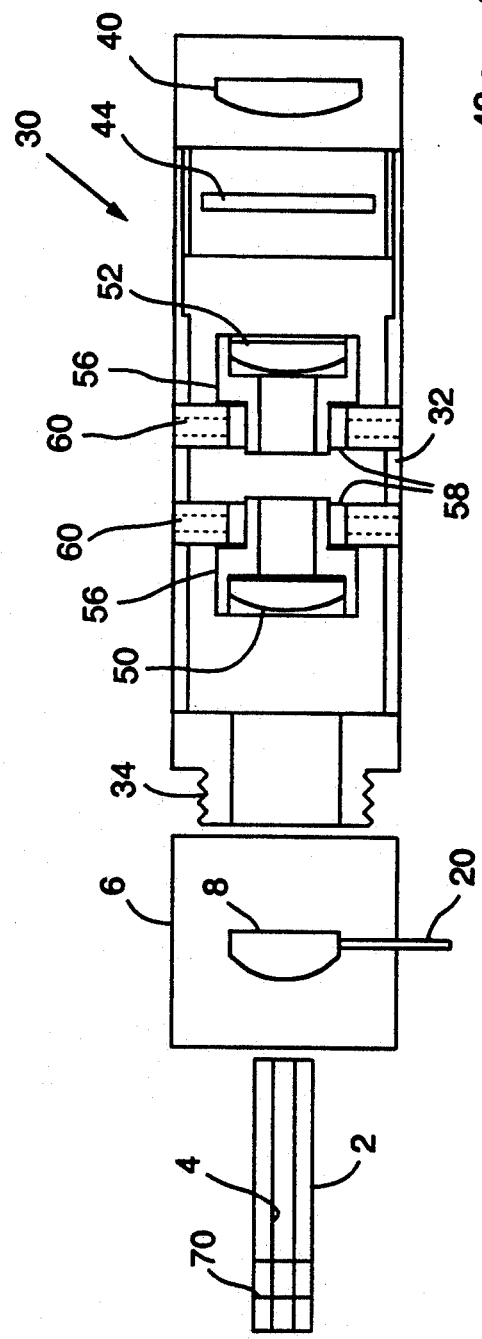
FIG. 2 is a cross section of the optical alignment tool of the subject invention shown in conjunction with a coupler and an endoscope.

Turning to FIG. 2 there is illustrated the alignment tool 30 of the subject invention. Tool 30 has a cylindrical housing 32 preferably formed from metal. One end of the housing includes a coupler 34 designed to mate either directly to the endoscope or to the intermediate coupler. Although there are many types of mating configurations, there are a few standards adopted by the manufacturers. It is within the scope of the subject invention to provide a coupler configuration 34 dimensioned to mate with the appropriate hardware.

The opposite end of the housing 32 is provided with a focusing eyepiece 40. In the preferred embodiment, the eyepiece is a standard 10× magnifier which can be obtained from Edmund Scientific, Part No. R37,692.

Figure 3:
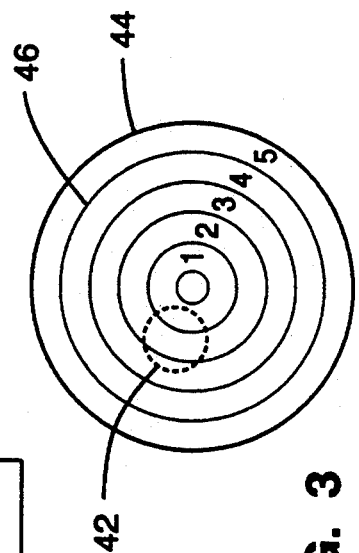
FIG. 3 is an end view of a preferred form of reticle.

The subject tool further includes a lens system for imaging the distal end 42 of the endoscope onto a reticle 44. As illustrated in FIG. 3, reticle 44 preferably includes plurality of radially concentric lines 46. These lines can be numbered for easy reference. A suitable reticle is available from Edmund Scientific, Part No. R51,034.

The selection of the optical elements for the lens system is dependent on a number of factors. Factors which must be considered include the desired length of the housing 32 as well as the length of the endoscope to evaluate. In an embodiment which has been constructed, the length of the housing is 63.5 mm and the lenses were selected to operate with endoscopes having a length ranging from about 13 to 17 inches. As illustrated in FIG. 2, lens 50 is a convex positive lens with a focal length of 38 mm. Lens 52 is a concave negative lens with a focal length of −43 mm. The separation between the lenses is 25 mm. The distance from lens 52 to the reticle is less critical and is on the order of 19 mm.

Each lens 50, 52 is mounted within a holder 56. The holders 56 are in turn mounted within adjustable yokes 58. Set screws 60 are provided to align the radial position of the lenses during assembly of the tool.

In use, tool 30 is preferably connected to the coupler of the endoscope. Alternatively, the tool can be connected to the endoscope itself, however, the lens 8 in the coupler provides a sharper image in the tool. The operator will then look into the eyepiece 40 to view the image of the distal end 42 of the endoscope 4 on the reticle as illustrated in dotted line in FIG. 3. To improve contrast, the distal end of endoscope should be directed to a light source or a white background. If the image is centered, it can be assumed that the endoscope and coupler are in axial alignment. When the image is off center as shown in FIG. 3, it can be assumed that the endoscope is misaligned. The extent of the radial displacement of the image gives an indication of the extent of axial misalignment of the endoscope.

If the endoscope is misaligned and has no adjustment capability it must be replaced. If however an adjustment mechanism is provided, the endoscope may be aligned using the subject tool. More specifically, the position of the joystick 20 can varied until the image of the distal end of the endoscope is centered on the reticle.

The sharpness of the image in the reticle can be further enhanced if the aperture at the distal end of the endoscope is restricted. More specifically, because the inner surface of the channel 4 tends to be highly reflecting, light entering the end will be reflected and scattered giving the image a more diffuse edge. Accordingly, the image can be improved by mounting a small tubular member 70 in the distal end of the bore. The tubular member 70 can be formed from dark plastic and be provided with axial cuts to allow flexing and variation in diameter. The inner diameter of member 70 is less than the diameter of the channel. Due to the reduced diameter and nonreflecting material of member 70, the image on the reticle will be much sharper.

As noted above, the subject tool can be quickly used by almost anyone to determine if the endoscope is aligned. If the endoscope is misaligned, the proper steps can be taken to correct the problem well before surgery is scheduled to begin.

While the subject invention has been described with reference to a preferred embodiment, various changes and modifications could be made therein, by one skilled in the art, without varying from the scope and spirit of the subject invention as defined by the appended claims.

We claim:

1. A tool for evaluating the optical alignment of an axially extending channel formed within an endoscope, said endoscope having proximal and distal ends, said endoscope comprising:
   a housing having opposed first and second ends, with said first end having a coupler means configured to mate with the proximal end of the endoscope;
   lens means located in said housing; and
   a reticle located in said housing between said lens means and said second end of the housing, said lens means for focusing an image of the distal end of the axially extending endoscope channel on the reticle such that in use, any misalignment of the endoscope channel will result in said image being radially misaligned from the center of the reticle.

2. A tool as recited in claim 1 wherein said lens means is defined by a lens pair including a positive and a negative lens.

3. A tool as recited in claim 1 wherein said reticle includes a plurality of radially concentric lines.

4. A tool as recited in claim 1 wherein the second end of the housing further includes an eyepiece.

5. A tool as recited in claim 4 wherein said eyepiece magnifies the image on the reticle by a factor of ten.

6. A tool as recited in claim 1 further including a tubular member for insertion into the channel at the distal end of the endoscope for limiting light into the channel so that said image on the reticle will be sharper.

* * * * *